(12) United States Patent
Patankar

(10) Patent No.: US 8,709,509 B2
(45) Date of Patent: Apr. 29, 2014

(54) HERBAL COMPOSITION FOR THE TREATMENT OF WOUND HEALING, A REGENERATIVE MEDICINE

(76) Inventor: Suresh Balkrishna Patankar, Pune (IN)

( * ) Notice: Subject to any disclaimer, the term of this patent is extended or adjusted under 35 U.S.C. 154(b) by 0 days.

(21) Appl. No.: 14/000,276

(22) PCT Filed: Feb. 17, 2012

(86) PCT No.: PCT/IN2012/000116
§ 371 (c)(1),
(2), (4) Date: Aug. 19, 2013

(87) PCT Pub. No.: WO2012/123962
PCT Pub. Date: Sep. 20, 2012

(65) Prior Publication Data
US 2013/0323337 A1 Dec. 5, 2013

(30) Foreign Application Priority Data
Feb. 17, 2011 (IN) .......................... 444/MUM/2011

(51) Int. Cl.
*A61K 36/00* (2006.01)
*A61K 36/9066* (2006.01)
*A61K 36/58* (2006.01)
*A61K 36/236* (2006.01)

(52) U.S. Cl.
USPC ........................ 424/725; 424/756; 424/757

(58) Field of Classification Search
None
See application file for complete search history.

(56) References Cited

U.S. PATENT DOCUMENTS

| 5,401,504 A | 3/1995 | Das et al. |
| 2010/0178367 A1 | 7/2010 | Saxena |

FOREIGN PATENT DOCUMENTS

| JP | 11199461 | 7/1999 |
| WO | 2005115090 | 12/2005 |
| WO | 2008072256 | 6/2008 |

OTHER PUBLICATIONS

"Database WPI", Week 199942 Thomson Scientific, London, GB; AN 1999-496806 XP002682578.
"impgc-International Medicinal Plants Growers' Consortium Indian Medicinal Plants Growers' Consortion : "Hamiltonia suaveolens Roxb."", XP002682579, Retrieved from the Internet: URL: http://www.impgc.com/plantinfo_A.php?id=423 [retrived on Aug. 19, 2013], 1990.
Biswas, et al., "Plant Medicines of Indian Origin for Wound Healing Activity: A Review", International Journal of Lower Extremity Wounds,, Sag Science Press. Thousand oaks, CA, US. vol. 2, No. 1, Jan. 1, 2003, 25-39.
Charde, et al., "Investigation on the wound healing activity of Tilvadi ghrita: a herbal formulation", Indian Journal of Traditional Knowledged REseources,, New Delhi-India, vol. 3, No. 3, Jul. 1, 2004, 247-252.
Sudeendra, Bhat et al., "Formulation and Evaluation of Polyherbal Wound Treatments", Asian Journal of Pharmaceutical Sciences vol. 2, No. 1 2007, 11-17.

*Primary Examiner* — Qiuwen Mi
(74) *Attorney, Agent, or Firm* — Kramer Amado, P.C.

(57) ABSTRACT

The present invention discloses a novel, synergistic, effective herbal composition as a regenerative medicine comprising combination therapeutically effective amounts of extracts obtained from *Curcuma longa, Glycyrrhiza glabara, Hamiltonia suaveolens, Typha angustifolia* and *Azadirachta indica*, along with optionally comprising Pig fat in *Sesamum indicum* (Til) oil as a base, useful for the treatment of wound healing. The present invention also discloses a process for preparation of said herbal composition.

27 Claims, 6 Drawing Sheets

Step –I Application of oil after surgery

Step –II Implantation of Tubing for oil application

Step-III Application of Oil through tubing

Step -IV Healing of stitches after 7th days

Step -V Complete healing of wound after 9th days

Diabetic foot wound

Lower lip ( Removal of buccal mucosa)

1st day  Control

8th day

1st day  Treatment group

8th day

Post TURP Control group
Six weeks post op.

Post TURP Treatment group
Six weeks post op.

Cont.

HERBAL COMPOSITION FOR THE TREATMENT OF WOUND HEALING, A REGENERATIVE MEDICINE

TECHNICAL FIELD OF THE INVENTION

The present invention relates to a novel synergistic and effective herbal composition as a regenerative medicine comprising combination of extracts obtained from *Curcuma longa, Glycyrrhiza glabara, Hamiltonia suaveolens, Typha angustifolia* and *Azadirachta indica* along with optionally pig fat in *Sesamum indicum* (Til) oil as a base; useful for the treatment of wound healing. The present invention also relates to a process for preparation of said herbal composition.

BACKGROUND OF THE INVENTION

Wound healing or wound repair, is an intricate process in which the skin (or another organ-tissue) repairs itself after injury. In normal skin, the epidermis (outermost layer) and dermis (inner or deeper layer) exists in steady-state equilibrium, forming a protective barrier against the external environment. Once the protective barrier is broken, the normal (physiologic) process of wound healing is immediately set in motion.

Types of Wound Healing:

The classic model of wound healing is divided into three or four sequential, yet overlapping, phases: (1) hemostasis (2) inflammatory (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active bleeding (hemostasis).

Categories of Wound Healing:

Category 1: Primary wound healing or healing by first intention occurs within hours of repairing a full-thickness surgical incision. This surgical insult results in the mortality of a minimal number of cellular constituents.

Category 2: If the wound edges are not re-approximated immediately, delayed primary wound healing transpires. This type of healing may be desired in the case of contaminated wounds. By the fourth day, phagocytosis of contaminated tissues is well underway, and the processes of epithelization, collagen deposition, and maturation are occurring. Foreign materials are walled off by macrophages that may metamorphose into epithelioid cells, which are encircled by mononuclear leukocytes, forming granulomas. Usually the wound is closed surgically at this juncture, and if the "cleansing" of the wound is incomplete, chronic inflammation can ensue, resulting in prominent scarring.

Category 3: A third type of healing is known as secondary healing or healing by secondary intention. In this type of healing, a full-thickness wound is allowed to close and heal. Secondary healing results in an inflammatory response that is more intense than with primary wound healing. In addition, a larger quantity of granulomatous tissue is fabricated because of the need for wound closure. Secondary healing results in pronounced contraction of wounds. Fibroblastic differentiation into myofibroblasts, which resemble contractile smooth muscle, is believed to contribute to wound contraction. These myofibroblasts are maximally present in the wound from the $10^{th}$-$21^{st}$ days.

Category 4: Epithelization is the process by which epithelial cells migrate and replicate via mitosis and traverse the wound. This occurs as part of the phases of wound healing, which are discussed in Sequence of Events in Wound Healing. In wounds that are partial thickness, involving only the epidermis and superficial dermis, epithelization is the predominant method by which healing occurs. Wound contracture is not a common component of this process if only the epidermis or epidermis and superficial dermis are involved.

Wound healing is a biological process that begins with trauma and ends with scar formation. The goals of wound care include reducing risk factors that inhibit wound healing, enhancing the healing process and lowering the incidence of wound infections. Many medicinal plants have been found useful in wound healing. Medicinal plants leads to find therapeutically useful compounds, thus more efforts should be made towards isolation and characterization of the active principles and elucidation of the relationship between structure and activity. The combination of traditional and modern knowledge can produce better drugs for wound healing.

*Sesamum indicum* L. is a member of family Pedaliaceae. *Sesamum indicum* (Sesame) oil and sesame seeds have been consumed by humans for thousands of years. The oil is used for massage and health treatments of the body (abhyanga and shirodhara) and teeth (oil pulling) in the ancient Indian Ayurvedic System. Ayurveda views sesame oil as the most viscous of the plant oils and believes it may pacify the health problems associated with Vata aggravation. Sesame seed Oil is naturally occurring, pale yellow oil obtained from the seeds of the plant which is highly nutritive as it is a rich source of natural oxidants such as sesamin and sesamol. The oil content of sesame seeds is between 45% and 54% and is primarily composed of oleic, linoleic, palmitic and stearic acids.

Pig fat also known as 'Lard' is commonly used in many cuisines as a cooking fat or shortening, or as a spread similar to butter. It is also used to manufacture soap. In the January, 2004 issue of The American Journal of Physiology, Spurlock and Kolapo Ajuwon, both of the Department of Animal Sciences and the Comparative Medicine Program, report that pig fat cells respond to infections by producing hormone-like proteins that regulate certain aspects of the body's immune response. However, the use of pig-fat in herbal preparation is not known.

According to ancient traditional ayurvedic knowledge Pig fat is considered as Vranropak (Wound Healing) and Vran shodhak (Help in regeneration of tissue during wound healing tissue) and snehan (Lubricant) properties.

*Curcuma longa* (Turmeric) is a rhizomatous herbaceous perennial plant of the ginger family, Zingiberaceae. It is native to tropical South Asia and needs temperatures between 20° C. and 30° C. and a considerable amount of annual rainfall to thrive. Plants are gathered annually for their rhizomes, and propagated from some of those rhizomes in the following season.

*Glycyrrhiza glabra* (Liquorice or licorice) is the root of *Glycyrrhiza glabra* from which a somewhat sweet flavour can be extracted. The liquorice plant is a legume (related to beans and peas) that is native to southern Europe and parts of Asia.

*Hamiltonia suaveolens* (Jeetsaya); *Hamiltonia suaveolens* belongs to the plant family Rubiace and Genus *Hamiltonia*

*Typha angustifolia* (Ramban tus) is a perennial herbaceous plant of genus *Typha*. This cattail is an "obligate wetland" species that is commonly found in the northern hemisphere in brackish location has been proposed that the species was introduced from Europe to North America. In North America, it is also thought to have been introduced from coastal to inland locations.

*Azadirachta indica* (Kadu Nimba) is a tree in the mahogany family Meliaceae. It is one of two species in the genus *Azadirachta*, and is native to India and Pakistan growing in tropical and semi-tropical regions. Its fruits and seeds are the source of neem oil.

An article titled "Investigation on the Wound Healing Activity of *Tilvadighrita*: A Herbal Formulation" by M S Charde et al., Indian journal of traditional knowledge 2004, 3 (3): 247-252, discloses a herbal formulation of *Sesamum indicum, Glycyrrhiza glabra* and Ghee for investigating the wound healing property employing incision and excision wound models in male rats.

An article titled "Formulation and Evaluation of Polyherbal Wound Treatments" by R. Sudeendra Bhat, J. Shankrappa and H. G. Shivakumar, Asian Journal of Pharmaceutical Sciences 2007, 2 (1): 11-17, discloses the evaluation of emulsifying ointment and carbopol 934 gel formulations containing extracts of *Azadirachta indica, Tridax procumbens* and *Curcuma longa* and the results obtained were suggest that gel-based formulations produced better wound healing than emulsifying ointment formulations.

US Publication No. 20100178367 relates to a herbal formulation with highly potent wound healing properties, in humans and animals. The composition consists of aqueous extracts of *Azadirachta indica*, in a mixture of natural oils along with herbs viz. *Berberis aristata, Curcuma longa, Glycyrrhiza glabra, Jasminum officinale, Picrorhiza kurrooa, Pongamia pinnata, Rubia cardifolia, Saussurea lappa, Terminalia chebula, Trichosanth esdioica,* Capsicum and Stellata wild in well-defined ratios. The invention also includes a process for preparing the formulation by extracting the water-soluble components from bark of *Azadirachta indica*.

U.S. Pat. No. 5,401,504 relates to a method of promoting healing of a wound by administering turmeric to a patient afflicted with the wound.

WO Publication No. 2005115090 relates to the composition consists of extracts of *Ficus bengalensis, Ficus religiosa, Ficus infectoria, Ficus racemosa* and *Azadirachta indica* with pharmaceutically acceptable carriers and excipients, which has potent antimicrobial and wound healing properties.

Thus, there are herbal compositions reported in the prior arts which are used to treat wound healing, but none of the prior art discusses the synergistic and effective herbal composition with pig fat for the treatment of wound healing. Further, the pig fat has not been reported as medicine so also there is no indication of use along with any herbal constituents, which is achieved by the present invention

SUMMARY OF THE INVENTION

In accordance with the above, the present invention discloses a novel synergistic and effective herbal composition as a regenerative medicine comprising combination of extracts obtained from *Curcuma longa* (Haldi) *Glycyrrhiza glabara* (Jeshthamadh), *Hamiltonia suaveolens* (Jeetsaya); *Typha angustifolia* (Rambantus) and *Azadirachta indica* (KaduNimba); along with optionally comprising pig fat in *Sesamum indicum* (Til) oil as a base; useful for the treatment of wound healing.

In another aspect, the present invention provides a process for preparation of said herbal composition.

In yet another aspect, the herbal composition of the present invention can be administered via oral or topical route or suppository or any other suitable route of administration, in the form of Kadha, Lepa, Swaras, Pak or also in the form of oil, ointment or jelly.

DETAILED DESCRIPTION OF THE INVENTION

Figure 1:
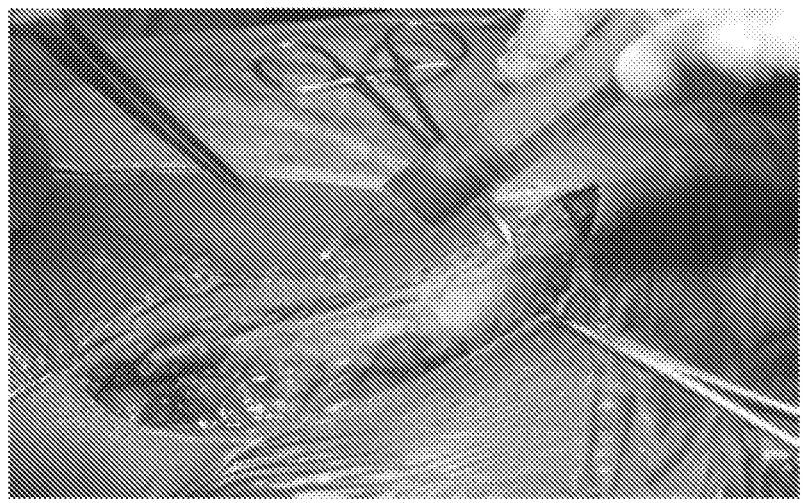
FIG. 1: Application of present herbal composition in Major Surgical Process (Topical Application 10 ml)
Figure 1:
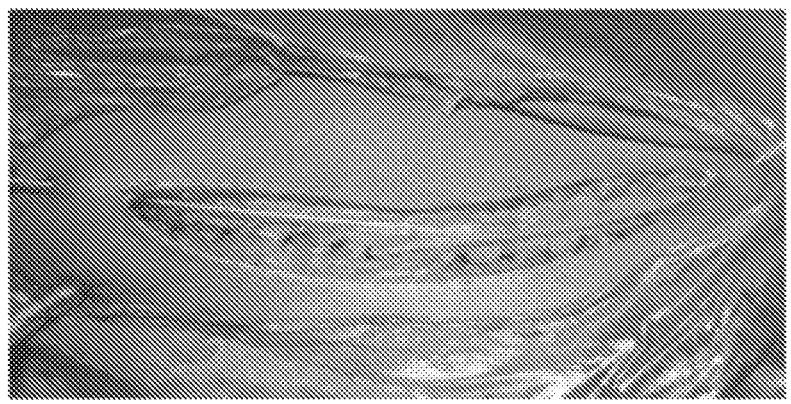
Figure 1A:
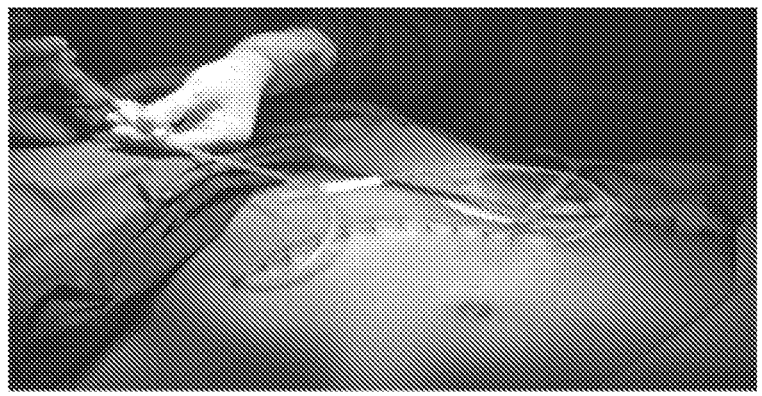
Figure 1A:
Figure 1A:
Figure 2:
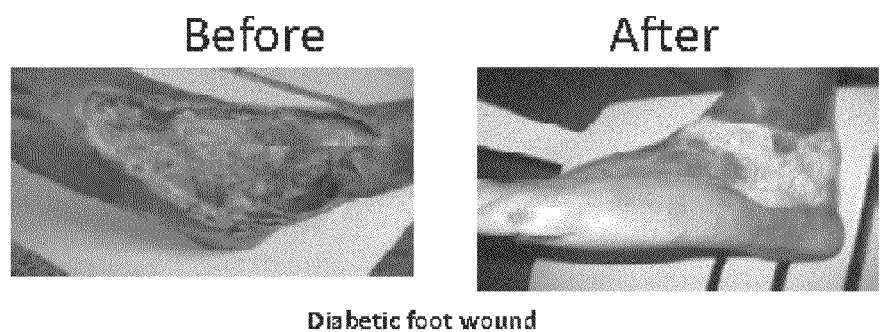
FIG. 2: Application of present herbal composition in Diabetic foot for 3 weeks 15 ml topical)
Figure 3:
FIG. 3: Application of present herbal composition on lower lip (Removal of buccul mucosa (5 ml topical)
Figure 3:
Figure 3:
Figure 3:
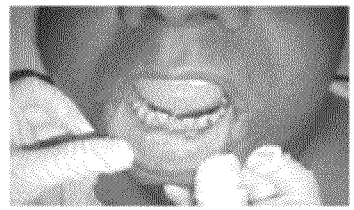
Figure 4:
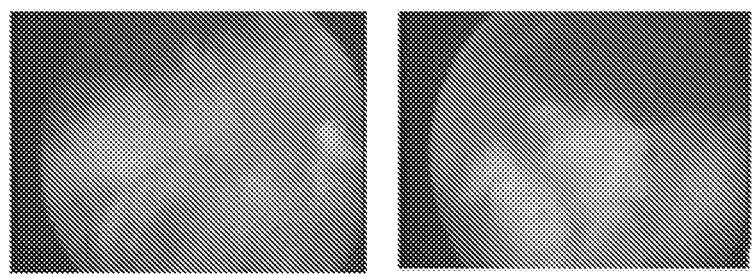
FIG. 4: Application of present herbal composition in endoscopic wounds (For Turp And Stricture Urethra Patients)
Figure 4:
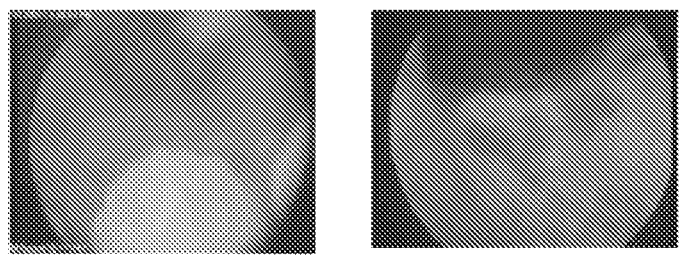
Figure 4:
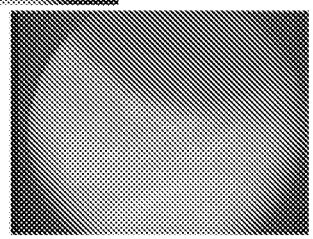
Figure 4A:
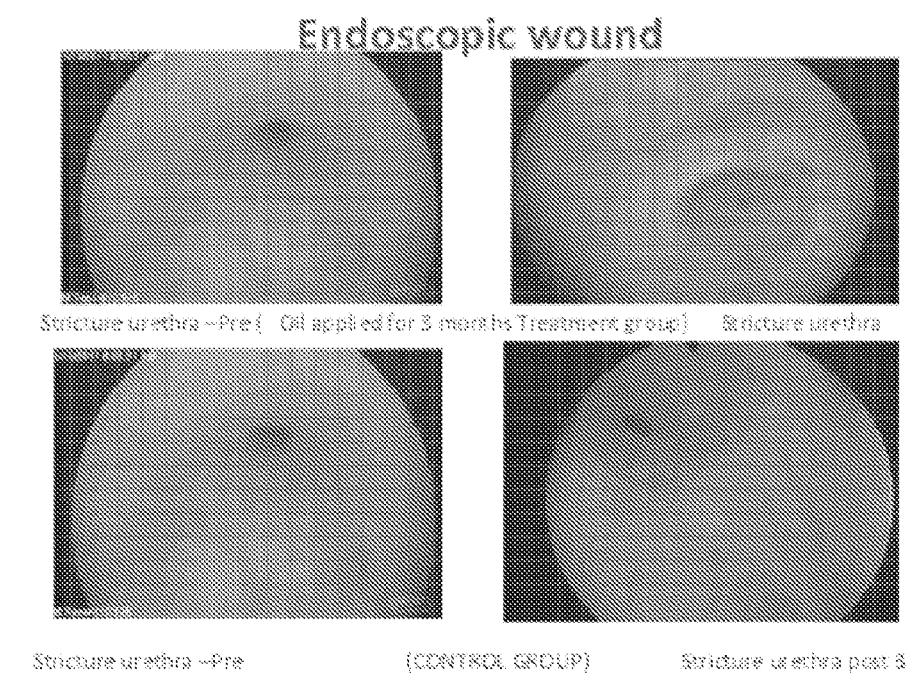

The invention will now be described in detail in connection with certain preferred and optional embodiments, so that various aspects thereof may be more fully understood and appreciated.

Definition of terms:

Kadha: Water extract of material

Lepa: Topical application of medicine usually it is in thick form

Swaras: Juice of Fresh material

Pak: Repeated treatment of extract to base

Source of the Plat Material:

The plant material used in the present invention i.e. *Curcuma longa* (Haldi) *Glycyrrhiza glabara* (Jeshthamadh), *Hamiltonia suaveolens* (Jeetsaya); *Typha angustifolia* (Rambantus) and *Azadirachta indica* are abundantly grown worldwide such as Southern Europe, Southeastern Australia, North America, Africa including India. Hence, the material was collected from any of the aforementioned source.

The appropriate part of the plant used in the composition of the present invention is given below:

| Sr. No. | Scientific Name | Common Name | Part Used in formulation |
|---|---|---|---|
| 1. | *Curcuma longa* | Haldi | Rhizome |
| 2. | *Glycyrrhiza glabara* | Jeshthamadh | Rhizome |
| 3. | *Hamiltonia suaveolens* | Jeetsaya | Stem bark |
| 4. | *Typha angustifolia* | Rambantus | Flowers |
| 5. | *Azadirachta indica* | Kadunimba | Leaf |
| 6. | *Sesamum ndicum* | Til (Oil as base) | Seeds |

In a preferred embodiment, the present invention describes a synergistic and effective herbal composition as a regenerative medicine comprising combination of therapeutically effective amount of extracts obtained from rhizomes of *Curcuma longa* & *Glycyrrhiza glabara*, Stem bark of *Hamiltonia suaveolens*; flower of *Typha angustifolia* and leaf of *Azadirachta indica* in *Sesamum indicum* (Til) oil as a base; along with optionally comprising pig fat, useful for the treatment of wound healing.

In a preferred embodiment, the present invention discloses a herbal composition as a regenerative medicine for the treatment of wound healing comprising, extracts of *Curcuma longa* in an amount of about 5 to 15%;

extracts of *Glycyrrhiza glabara* in an amount of about 2 to 30%;

extracts of *Hamiltonia suaveolens* in an amount of about 2 to 50%;

extracts of *Typha angustifolia* in an amount of about 1 to 50%;

extracts of *Azadirachta indica* in an amount of about 0.5 to 30% and

*Sesamum indicum* oil as a base in an amount of about 20 to 60% of the total composition.

In another embodiment, the present invention discloses a herbal composition as a regenerative medicine for the treatment of wound healing comprising,
extracts of *Curcuma longa* in an amount of about 7 to 13%;
extracts of *Glycyrrhiza glabara* in an amount of about 5 to 20%;
extracts of *Hamiltonia suaveolens* in an amount of about 5 to 30%;
extracts of *Typha angustifolia* in an amount of about 2 to 40%;
extracts of *Azadirachta indica* in an amount of about 1 to 25% and
*Sesamum indicum* oil as a base in an amount of about 25 to 55% of the total composition.

In another embodiment, the present invention discloses a herbal composition as a regenerative medicine for the treatment of wound healing comprising,
extracts of *Curcuma longa* in an amount of about 10 to 12%;
extracts of *Glycyrrhiza glabara* in an amount of about 8 to 15%;
extracts of *Hamiltonia suaveolens* in an amount of about 8 to 15%;
extracts of *Typha angustifolia* in an amount of about 3 to 35%;
extracts of *Azadirachta indica* in an amount of about 2 to 20% and
*Sesamum indicum* oil as a base in an amount of about 40 to 50% of the total composition.

In another embodiment, the present invention discloses a herbal composition as a regenerative medicine for the treatment of wound healing comprising,
extracts of *Curcuma longa* in an amount of 11.3%;
extracts of *Glycyrrhiza glabara* in an amount of about 11.3%;
extracts of *Hamiltonia suaveolens* in an amount of about 11.3%;
extracts of *Typha angustifolia* in an amount of about 5.8%;
extracts of *Azadirachta indica* in an amount of about 3% and
*Sesamum indicum* oil as a base in an amount of about 46% of the total composition.

In another preferred embodiment, the present invention discloses a herbal composition as a regenerative medicine for the treatment of wound healing comprising,
extracts of *Curcuma longa* in an amount of about 5 to 15%;
extracts of *Glycyrrhiza glabara* in an amount of about 2 to 30%;
extracts of *Hamiltonia suaveolens* in an amount of about 2 to 50%;
extracts of *Typha angustifolia* in an amount of about 1 to 50%;
extracts of *Azadirachta indica* in an amount of about 0.5 to 30%
*Sesamum indicum* oil as a base in an amount of about 20 to 60%; and
Pig fat in an amount of about 2% to 30% of the total composition.

In another embodiment, the present invention discloses a herbal composition as a regenerative medicine for the treatment of wound healing comprising,
extracts of *Curcuma longa* in an amount of about 7 to 13%;
extracts of *Glycyrrhiza glabara* in an amount of about 5 to 20%;
extracts of *Hamiltonia suaveolens* in an amount of about 5 to 30%;
extracts of *Typha angustifolia* in an amount of about 2 to 40%;
extracts of *Azadirachta indica* in an amount of about 1 to 25%;
*Sesamum indicum* oil as a base in an amount of about 25 to 55% and
Pig fat in an amount of about 5 to 25% of the total composition.

In another embodiment, the present invention discloses a herbal composition as a regenerative medicine for the treatment of wound healing comprising,
extracts of *Curcuma longa* in an amount of about 10 to 12%;
extracts of *Glycyrrhiza glabara* in an amount of about 8 to 15%;
extracts of *Hamiltonia suaveolens* in an amount of about 8 to 15%;
extracts of *Typha angustifolia* in an amount of about 3 to 35%;
extracts of *Azadirachta indica* in an amount of about 2 to 20%;
*Sesamum indicum* oil as a base in an amount of about 40 to 50% and
Pig fat in an amount of about 10 to 20% of the total composition.

In another embodiment, the present invention discloses a herbal composition as a regenerative medicine for the treatment of wound healing comprising,
extracts of *Curcuma longa* in an amount of 11.3%;
extracts of *Glycyrrhiza glabara* in an amount of about 11.3%;
extracts of *Hamiltonia suaveolens* in an amount of about 11.3%;
extracts of *Typha angustifolia* in an amount of about 5.8%;
extracts of *Azadirachta indica* in an amount of about 3%;
*Sesamum indicum* oil as a base in an amount of about 46% and
Pig fat in an amount of about 11.3% of the total composition.

In yet another preferred embodiment, the present invention discloses herbal composition as a regenerative medicine for the treatment of wound healing comprising,
extracts of *Hamiltonia suaveolens* in an amount of about 2 to 50%; and
extracts of *Typha angustifolia* in an amount of about 1 to 50%; of the total composition In yet another preferred embodiment, the present invention discloses herbal composition as a regenerative medicine for the treatment of wound healing comprising,
extracts of *Hamiltonia suaveolens* in an amount of about 2 to 50%;
extracts of *Typha angustifolia* in an amount of about 1 to 50%; and
*Sesamum indicum* oil as a base in an amount of 20 to 60% of the total composition.

In yet another preferred embodiment, the present invention discloses herbal composition as a regenerative medicine for the treatment of wound healing comprising,
extracts of *Hamiltonia suaveolens* in an amount of about 2 to 50%;
extracts of *Typha angustifolia* in an amount of about 1 to 50%;
*Sesamum indicum* oil as a base in an amount of 20 to 60% and
Pig fat in an amount of about 2% to 30% of the total composition.

The extracts used in the present invention for preparation of the herbal composition are derived from various parts of the plant such as rhizomes, stem bark, flowers and leaves that are extracted using conventional solvents like water, alcohols and hydro-alcohols or any other organic solvents that are suitable to obtain complete extract of the herbs.

The herbal composition of the present invention is formulated in the form Kadha, Lepa, Swaras, Pak and also in the form of oil, ointment or jelly.

The herbal composition of the present invention is administered via oral or topical route or suppository or any other suitable route of administration.

The recommended dose of the present herbal composition via oral administration is 1.5 to 15 ml per day The recommended dose of the present herbal composition via topical administration is 2 to 20 ml per day.

In another embodiment, the present invention describes an effective herbal composition as a regenerative medicine for the treatment of open wounds like bed sores, burns, diabetic foot, post-operative wounds, leg ulcers, lower lip wounds, penile ulcers, urethral, scrotal, abdominal wounds and endoscopic wounds like prostate and urethral stricture wounds.

In another embodiment, the herbal extracts used in the present invention are prepared as follows:

The herbal extracts of *Curcuma longa* (Haldi) and *Glycyrrhiza glabara* (Jeshthamadh) is prepared by mixing rhizomes of *Curcuma longa* and *Glycyrrhiza glabara* in 20-30 vol. of water followed by heating at temperature of 80 to 95° C. The extract obtained is evaporated to one third quantity The herbal extracts of *Hamiltonia suaveolens* (Jeetsaya) is prepared by mixing stem bark of *Hamiltonia suaveolens* in 15-20 vol. of water followed by heating at temperature of 80 to 95° C. The extract obtained is evaporated to one fourth quantity The herbal extracts of *Typhaangusti folia* (Rambantus) is prepared by mixing flowers of *Typha angustifolia* in 20 vol. of water followed by heating at temperature of 80 to 95° C. The extract obtained is evaporated to one fifth quantity The herbal extracts of *Azadirachta india* (KaduNimba) is prepared by crushing and churning the fresh leaves of *Azadirachta india* (KaduNimba) to obtained juice.

The pig fat as is processed by heating the same with *Sesamum indicum* (Til) oil between the temperature of 60 to 95° C.

Sesame seed oil used is naturally occurring, pale yellow oil obtained from the seeds of the plant.

In another preferred embodiment, the invention provides the process for preparation of herbal composition of the present invention (With pig fat), wherein said process comprises following steps:— a) Mixing *Sesamum indicum* (Til) oil and Pig Fat in the ratio of 4:1;
b) combining and adding extracts of *Curcuma longa* (Haldi) and *Glycyrrhiza glabara* (Jeshthamadh) in the ratio of 1:1 to step (a);
c) adding extracts of *Hamiltonia suaveolens* (Jeetsaya) in the ratio of 1:5 to step (a);
d) adding extract of *Typha angustifolia* (Ramban tus) in the ratio of 1:10 to step (a);
e) preparing *Azadirachta india* (Kadu Nimba) Swaras (Juice) and is adding in the ratio of 1:5 to step (a) to obtain a mixture consisting of;
   Sesamum indicum (Til) oil and pig fat in 5 parts, *Curcuma longa* (Haldi) in 1 part and *Glycyrrhiza glabara* (Jeshthamadh) in 1 part, *Hamiltonia suaveolens* (Jeetsaya) in 1 part, *Typha angustifolia* (Ramban tus) in 0.5 part, *Azadirachta india* (Kadu Nimba) Swaras (Juice) in 1 part.
f) evaporating the mixture of step (e) till the water is completely removed to obtain final formulation;
g) fortifying the above formulation of step (f) 11 times using same herbal extracts in same proportions.

In yet another embodiment, the invention provides process for preparation of the herbal composition of the present invention (Without Pig fat), wherein said process comprises following steps:— a) Combining the extracts of *Curcuma longa* (Haldi) and *Glycyrrhiza glabara* (Jeshthamadh) and is taken in the ratio of 1:1;
b) mixing the combined extracts of *Curcuma longa* (Haldi) and *Glycyrrhiza glabara* (Jeshthamadh) of step 1 in *Sesamum indicum* (Til) oil in the ratio of 1:5;
c) adding extract of *Hamiltonia suaveolens* (Jeetsaya) in the ratio of 1:5 to step (b);
d) adding extract of *Typha angustifolia* (Ramban tus) in the ratio of 1:10 to step (b);
e) preparing *Azadirachta india* (Kadu Nimba) Swaras (Juice) and adding in the ratio of 1:5 to step (b) to obtain a mixture consisting of;
   Sesamum indicum (Til) oil in 5 parts, *Curcuma longa* (Haldi) in 1 part and *Glycyrrhiza glabara* (Jeshthamadh) in 1 part, *Hamiltonia suaveolens* (Jeetsaya) in 1 part, *Typha angustifolia* (Ramban tus) in 0.5 part, *Azadirachta india* (Kadu Nimba) Swaras (Juice) in 1 part;
f) evaporating the mixture of step (e) till the water is completely removed to obtain final formulation;
g) fortifying the above formulation of step (f) 11 times using same herbal extracts in same proportions.

In yet another embodiment, the present invention provides a method of treating a subject suffering wound healing, with herbal composition of the present invention; wherein the subject is mammal, preferably, human.

In yet another embodiment, the present invention provides the use of herbal composition of the present invention to treat different types of wound healing such as open wounds like bed sores, burns, diabetic foot, post-operative wounds, leg ulcers, lower lip wounds, penile ulcers, urethral, scrotal, abdominal wounds and endoscopic wounds like prostate and urethral stricture wounds.

All the ingredients of synergistic and effective herbal composition of the present invention are well standardized with acceptable impurity profiles. All the ingredients were reported to be safe in literature. Further, the product of the present invention has been proven to be safe. The safety and clinical efficacy of the composition is proved on humans with effective wound healing.

Clinical Study:

Preclinical Efficacy of Present Herbal Composition:

The present herbal composition was subjected to preclinical study to understand underlying mechanism of action for wound healing activity. This study was carried out by standard models to evaluate wound healing activity like Incision, Excision and dead space wound models in laboratory animals. While conducting these studies various biochemical parameters and histological studies of wound tissue were carried out to explore the underline mechanism of action.

In the process of wound healing a formation of protective layer scab is the initial event resulting in the formation of blood clot due to combination of platelets and fibrin. In the histological observations of wound tissue under microscope revealed, that there was significant scab formation, in the animals treated with present herbal composition as compare to animals from control groups. As far as cellular events are concern, there was significant fibroblast proliferation as well as neo vascularization in the groups treated with present herbal composition in comparison to control animals. There was less inflammation in the animals treated with present herbal composition as compare to control animals. This may be due to presence of *Curcuma longa* and *Glycyrrhiza glabra*, which are ingredients of the present herbal composition which are known for anti-inflammatory activity. Usually for rapid healing anti-inflammatory activity is essential, as it provides shortening of healing process. In the animals treated with present herbal composition there was significant deposition of collagen in granular tissue, which provides strength and integrity to tissue matrix during wound healing process. Generally to determine turnover of collagen, the estimation of hydroxproline is carried out, which is a breakdown product of collagen. There was a significantly higher level of Collagen as well as Hydroxproline indicating more synthesis and turnover of Collagen during the process of wound healing due to present herbal composition. Further to this also, in the final stage of wound healing remodeling which is resulted due to regaining its strength and elasticity through reorganization of collagen and elastic fibers for reconstruction of dermis. In this stage also there was significantly more activity in the animals treated with present herbal composition. Thus, present herbal composition is exhibiting wound healing activity through promoting various stages in general and promoting formation as well as turnover of collagen, which is playing important role in the process of healing of tissue in particular.

Preclinical Safety Profiles of the Present Herbal Composition:

1. Acute Dermal Toxicity Study—The acute dermal safety of present herbal composition with and without fat formulations were evaluated by employing OECD guidelines Number 434, adopted on 14 May 2004 using Albino rats. This study was carried out by employing 2000 mg/kg a limit dose by dermal application protocol and observing for 14 days for general health, behavioral changes and mortality. All animals were normal without any effect on health, behavior with no mortality indicating safety of the present herbal composition with and without fat formulations by acute dermal application up to 2000 mg/kg dose.

2. Mucus Membrane Irritation Test—The mucus membrane irritation test for present herbal composition, with and without fat were evaluated by employing OECD guidelines Number 405, adopted on 17 Jul. 1992 using New Zealand albino rabbits. The formulations 0.10 ml were applied on mucus membrane and observed for erythema and edema for 7 days. Both the compositions of present invention with and without fat were safe on mucus membrane.

3. Sub-Acute Toxicity Test—The repeated dermal application of 1000 mg/kg of the present herbal composition with and without fat for 28 days was carried out by employing OECD guidelines number 410 in albino rats. There was no itching, redness, flare and inflammation at the site of application. The animals were normal without any change in their behavioral pattern and there was no mortality. There was no significant difference in the food consumption and body weigh changes in animals. There was no difference in various blood parameters like Hb, PCV, RBC, WBC total and differential count, SGPT, SGOT, ALP, Total proteins, Glucose, urea as well as urine parameters like Sp.gr., pH, Protein, Glucose, Ketones (Qualitative), microscopy parameters like PC, RBC, EC, Cr, Cast in comparison to control animals. There was NO significant difference in the absolute and relative weights of various organs like brain, lung, heart, liver, spleen, kidney, adrenals, testis/ovaries. There was no difference in gross necropsy and histology of liver, kidney and skin samples. Thus, indicating safety of present herbal composition by dermal application at the dose of 1000 mg/kg for 28 days.

Clinical Studies of Herbal Composition of Present Invention on Various Types of Wound Patients:

1. Endoscopic Wounds:
    a) Transurethral resection of the prostate (TURP), is considered as the reference standard for the surgical treatment of symptomatic Benign Prostatic Hyperplasia (BPH) and represents one of the most common operations. The present herbal composition was tried in above patients to understand the advantage of its wound healing property. Clinically this study was carried out in 56 BPH cases and the observations in the patients treated with present herbal composition are less dysuria, frequency and urgency, rapid healing with less pain.
    b) Urethral Stricture: The term urethral stricture refers to anterior urethral disease, or a scarring process involving the spongy erectile tissue of the corpus spongiosum (Spongiofibrosis). Contraction of this scar reduces the urethral lumen leading to acute urinary retention, straining to void, splaying of the urinary stream and infections of the urinary tract, including recurrent epididymitis and prostatitis in this condition there is no alternative than to go for surgical procedure. The present herbal composition was used in these cases and out of 29 cases 7 cases have shown significant improvement in above symptoms.

2. Open Surgical Wounds:
    Clinically the present herbal composition was explored in more than 100 patients consisting of A V Fistula, Circumcision, Open Plyloplasty, Hand A. V. Fistula [LT], Distal hypospadias, Single Stage Repair, B/L Inguinal Dissection Cystoscopy Uretric Cathetiration Open partial Nephrectomy, Epididymal, Cyst Removal, Congenital Inguino Scrotal Swelling etc. It was observed that 77 cases showed promising wound healing, with primary intention without any incidence of infection. There was no edema, less pain and fast wound healing was observed.

3. In open wounds like bed sores, burns, diabetic foot, leg ulcers, lower lip wounds, penile ulcers, urethral, scrotal, abdominal wounds total 40 patients were treated with present herbal composition which showed faster healing without any infections and less or no scar.

The following examples, which include preferred embodiments, will serve to illustrate the practice of this invention, it being understood that the particulars shown are by way of example and for purpose of illustrative discussion of preferred embodiments of the invention.

EXAMPLE

Example 1

| Botanical Name | Common Name | Part use | Range |
|---|---|---|---|
| Sesamum indicum | Til oil | Seed | 20% to 60% |
| Curcuma longa | Haldi | Rhizome | 5% to 15% |
| Glycyrrhiza glabara | Jeshthamadh | Rhizome | 2% to 30% |
| Hamiltonia suaveolens | Jeetsaya | Stem bark | 2% to 50% |
| Typha angustifolia | Ramban tus | Flower | 1% to 50% |
| Azadirachta indica | Kadu Nimba | Leaf | 0.5% to 30% |
| Purified Water | * | * | Q.S. |

Example 2

| Botanical Name | Common Name | Part use | Range |
|---|---|---|---|
| Sesamum indicum | Til oil | Seed | 25 to 55% |
| Curcuma longa | Haldi | Rhizome | 7 to 13% |
| Glycyrrhiza glabara | Jeshthamadh | Rhizome | 5 to 20% |
| Hamiltonia suaveolens | Jeetsaya | Stem bark | 5 to 30% |
| Typha angustifolia | Ramban tus | Flower | 2 to 40% |
| Azadirachta indica | Kadu Nimba | Leaf | 1 to 25% |
| Purified Water | * | * | Q.S. |

Example 3

| Botanical Name | Common Name | Part use | Range |
|---|---|---|---|
| Sesamum indicum | Til oil | Seed | 40 to 50% |
| Curcuma longa | Haldi | Rhizome | 10 to 12% |
| Glycyrrhiza glabara | Jeshthamadh | Rhizome | 8 to 15% |
| Hamiltonia suaveolens | Jeetsaya | Stem bark | 8 to 15% |
| Typha angustifolia | Ramban tus | Flower | 3 to 35% |
| Azadirachta indica | Kadu Nimba | Leaf | 2 to 20% |
| Purified Water | * | * | Q.S. |

Example 4

| Botanical Name | Common Name | Part used | Quantity |
|---|---|---|---|
| Sesamum indicum | Til oil | Seed | 46% |
| Curcuma longa | Haldi | Rhizome | 11.3% |
| Glycyrrhiza glabara | Jeshthamadh | Rhizome | 11.3% |
| Hamiltonia suaveolens | Jeetsaya | Stem bark | 11.3% |
| Typha angustifolia | Ramban tus | Flower | 5.8% |
| Azadirachta indica | Kadu Nimba | Leaf | 3% |
| Purified Water | * | * | Q.S. |

Example 5

| Botanical Name | Common Name | Part used | Range |
|---|---|---|---|
| Sesamum indicum | Til oil | Seed | 20% to 60% |
| * | Pig Fat | * | 2% to 30% |
| Curcuma longa | Haldi | Rhizome | 5% to 15% |
| Glycyrrhiza glabara | Jeshthamadh | Rhizome | 2% to 30% |
| Hamiltonia suaveolens | Jeetsaya | Stem bark | 2% to 50% |
| Typha angustifolia | Ramban tus | Flower | 1% to 50% |
| Azadirachta indica | Kadu Nimba | Leaf | 0.5% to 30% |
| Purified Water | * | * | Q.S. |

Example 6

| Botanical Name | Common Name | Part used | Range |
|---|---|---|---|
| Sesamum indicum | Til oil | Seed | 25 to 55% |
| * | Pig Fat | * | 5 to 25% |
| Curcuma longa | Haldi | Rhizome | 7 to 13% |
| Glycyrrhiza glabara | Jeshthamadh | Rhizome | 5 to 20% |
| Hamiltonia suaveolens | Jeetsaya | Stem bark | 5 to 30% |
| Typha angustifolia | Ramban tus | Flower | 2 to 40%; |
| Azadirachta indica | Kadu Nimba | Leaf | 1 to 25%; |
| Purified Water | * | * | Q.S. |

Example 7

| Botanical Name | Common Name | Part used | Range |
|---|---|---|---|
| Sesamum indicum | Til oil | Seed | 40 to 50% |
| * | Pig Fat | * | 10 to 20% |
| Curcuma longa | Haldi | Rhizome | 10 to 12% |
| Glycyrrhiza glabara | Jeshthamadh | Rhizome | 8 to 15% |
| Hamiltonia suaveolens | Jeetsaya | Stem bark | 8 to 15% |
| Typha angustifolia | Ramban tus | Flower | 3 to 35% |
| Azadirachta indica | Kadu Nimba | Leaf | 2 to 20% |
| Purified Water | * | * | Q.S. |

Example 8

| Botanical Name | Common Name | Part used | Quantity |
|---|---|---|---|
| Sesamum indicum | Til oil | Seed | 46% |
| * | Pig Fat | * | 11.3% |
| Curcuma longa | Haldi | Rhizome | 11.3% |
| Glycyrrhiza glabara | Jeshthamadh | Rhizome | 11.3% |
| Hamiltonia suaveolens | Jeetsaya | Stem bark | 11.3% |
| Typha angustifolia | Ramban tus | Flower | 5.8% |
| Azadirachta indica | Kadu Nimba | Leaf | 3% |
| Purified Water | * | * | Q.S. |

Example 9

| Botanical Name | Common Name | Part used | Quantity |
|---|---|---|---|
| Sesamum indicum | Til oil | Seed | 20 to 60% |
| * | Pig Fat | * | 2% to 30% |
| Hamiltonia suaveolens | Jeetsaya | Stem bark | 2 to 50% |
| Typha angustifolia | Ramban tus | Flower | 1 to 50% |
| Purified Water | * | * | Q.S. |

Example 10

| Botanical Name | Common Name | Part used | Quantity |
|---|---|---|---|
| Sesamum indicum | Til oil | Seed | 20 to 60% |
| Hamiltonia suaveolens | Jeetsaya | Stem bark | 2 to 50% |
| Typha angustifolia | Ramban tus | Flower | 1 to 50% |
| Purified Water | * | * | Q.S. |

Example 11

| Botanical Name | Common Name | Part used | Quantity |
|---|---|---|---|
| Hamiltonia suaveolens | Jeetsaya | Stem bark | 2 to 50% |
| Typha angustifolia | Ramban tus | Flower | 1 to 50% |
| Purified Water | * | * | Q.S. |

I claim:

1. An herbal composition as a regenerative medicine for the treatment of wound healing comprising, extracts of *Curcuma longa* in an amount of about 5 to 15%;
   extracts of *Glycyrrhiza glabra* in an amount of about 2 to 30%;
   extracts of *Hamiltonia suaveolens* in an amount of about 2 to 50%;
   extracts of *Typha angustifolia* in an amount of about 1 to 50%; and
   extracts of *Azadirachta indica* in an amount of about 0.5 to 30% of the total composition.

2. The herbal composition as claimed in claim 1, wherein said composition further comprises *Sesamum indicum* oil as a base.

3. The herbal composition as claimed in claim 2, wherein *Sesamum indicum* oil is present in an amount of about 20 to 60% of the total composition.

4. The herbal composition as claimed in claim 3, wherein said composition comprises,
   extracts of *Curcuma longa* in an amount of about 7 to 13%;
   extracts of *Glycyrrhiza glabra* in an amount of about 5 to 20%;
   extracts of *Hamiltonia suaveolens* in an amount of about 5 to 30%;
   extracts of *Typha angustifolia* in an amount of about 2 to 40%;
   extracts of *Azadirachta indica* in an amount of about 1 to 25% and *Sesamun indicaum* oil as a base in an amount of about 25 to 55% of the total composition.

5. The herbal composition as claimed in claim 3, wherein said composition comprises,
   extracts of *Curcuma longa* in an amount of about 10 to 12%;
   extracts of *Glycyrrhiza glabra* in an amount of about 8 to 15%;
   extracts of *Hamiltonia suaveolens* in an amount of about 8 to 15%;
   extracts of *Typha angustifolia* in an amount of about 3 to 35%;
   extracts of *Azadirachta indica* in an amount of about 2 to 20% and *Sesamum indicum* oil as a base in an amount of about 40 to 50% of the total composition.

6. The herbal composition as claimed in claim 1, wherein said composition comprises,
   extracts of *Curcuma longa* in an amount of 11.3%;
   extracts of *Glycyrrhiza glabra* in an amount of about 11.3%;
   extracts of *Hamiltonia suaveolens* in an amount of about 11.3%;
   extracts of *Typha angustifolia* in an amount of about 5.8%;
   extracts of *Azadirachta indica* in an amount of about 3% and *Sesamum indicum* oil as a base in an amount of about 46% of the total composition.

7. An herbal composition as a regenerative medicine for the treatment of wound healing comprising,
   extracts of *Curcuma longa* in an amount of about 5 to 15%;
   extracts of *Glycyrrhiza glabra* in an amount of about 2 to 30%;
   extracts of *Hamiltonia suaveolens* in an amount of about 2 to 50%;
   extracts of *Typha angustifolia* in an amount of about 1 to 50%;
   extracts of *Azadirachta indica* in an amount of about 0.5 to 30% and
   Pig fat in an amount of about 2% to 30% of the total composition.

8. The herbal composition as claimed in claim 7, wherein said composition further comprises *Sesamum indicum* oil as a base.

9. The herbal composition as claimed in claim 8, wherein *Sesamum indicum* oil is present in an amount of about 20 to 60% of the total composition.

10. The herbal composition as claimed in claim 9, wherein said composition comprises,
    extracts of *Curcuma longs* in an amount of about 7 to 13%;
    extracts of *Glycyrrhiza glabra* in an amount of about 5 to 20%;
    extracts of *Hamiltonia suaveolens* in an amount of about 5 to 30%;
    extracts of *Typha angustifolla* in an amount of about 2 to 40%;
    extracts of *Azadirachta Indica* in an amount of about 1 to 25%;
    *Sesamum indicum* oil as a base in an amount of about 25 to 55% and
    Pig fat in an amount of about 5 to 25% of the total composition.

11. The herbal composition as claimed in claim 9, wherein said composition comprises,
    extracts of *Curcuma longs* in an amount of about 10 to 12%;
    extracts of *Glycyrrhiza glabra* in an amount of about 8 to 15%;
    extracts of *Hamiltonia suaveolens* in an amount of about 8 to 15%;
    extracts of *Typha angustifolla* in an amount of about 3 to 35%;
    extracts of *Azadirachta indica* in an amount of about 2 to 20%;
    *Sesamum indicum* oil as a base in an amount of about 40 to 50% and
    Pig fat in an amount of about 10 to 20% of the total composition.

12. The herbal composition as claimed in claim 9, wherein said composition comprises,
    extracts of *Curcuma glabra* in an amount of 11.3%;
    extracts of *Glycyrrhiza glabra* in an amount of about 11.3%;
    extracts of *Hamiltonia suaveoalens* in an amount of about 11.3%;
    extracts of *Typha angustifolia* in an amount of about 5.8%;
    extracts of *Azadirachta indica* in an amount of about 3%;
    *Sesamum indicum* oil as a base in an amount of about 46%; and
    Pig fat in an amount of about 11.3% of the total composition.

13. An herbal composition as a regenerative medicine for the treatment of wound healing comprising, extracts of *Hamiltonia sua veolens* in an amount of about 2 to 50% and extracts of *Typha angustifolia* in an amount of about 1 to 50% of the total composition.

14. The herbal composition as claimed in claim 13, wherein said composition further comprises *Sesamum indicum* oil as a base.

15. The herbal composition as claimed in claim 14, wherein *Sesamum indicum* oil is present in an amount of about 20 to 60% of the total composition.

16. An herbal composition as a regenerative medicine for the treatment of wound healing comprising,
    extracts of *Hamiltonia suaveolens* in an amount of about 2 to 50%;
    extracts of *Typha angustifolia* in an amount of about 1 to 50% and Pig fat in an amount of about 2% to 30% of the total composition.

17. The herbal composition as claimed in claim 16, wherein said composition further comprises *Sesamum indicum* oil as a base.

18. The herbal composition as claimed in claim 17, wherein *Sesamum indicum* oil is present in an amount of about 20 to 60% of the total composition.

19. The herbal composition according to claim 1, wherein the extracts are derived from various parts of the plant including rhizomes, stem bark, flowers and leaves that are extracted using conventional solvents.

20. The herbal composition according to claim 19, wherein the conventional solvents are selected from water, alcohols and hydro-alcohols or any other organic solvents that are suitable to obtain complete extract of the herbs.

21. The herbal composition according to claim 1, wherein said composition is administered via oral or topical route or suppository or any other suitable route of administration.

22. The herbal composition according to claim 1, wherein said composition is formulated in the form of in the form of oil, ointment or jelly.

23. A process for preparation of herbal composition according to claims 2, comprises,
   a) Combining the extracts of *Curcuma longa* and *Glycyrrhiza glabra* and is taken in the ratio of 1:1;
   b) mixing the combined extracts of *Curcuma longa* and *Glycyrrhiza glabra* of step a) in *Sesamum indicum* oil in the ratio of 1:5;
   c) adding extract of *Hamiltonia suaveolens* in the ratio of 1:5 to step (b);
   d) adding extract of *Typha angustifolia* in the ratio of 1:10 to step (b);
   e) preparing *Azadirachta India* and adding in the ratio of 1:5 to step (b) to obtain a mixture consisting of;
   *Sesamum indicurn* oil in 5 parts, *Curcuma longa* in 1 part and *Glycyrrhiza glabra* in 1 part, *Hamiltonia suaveolens* (Jeetsaya) in 1 part, *Typha angustifolia* in 0.5 part, *Azadirachta India* juice in 1 part;
   f) evaporating the mixture of step (e) till the water is completely removed to obtain final formulation;
   g) fortifying the above formulation of step (f) 11 times using same herbal extracts in same proportions.

24. A process for preparation of herbal composition according to claims 8 comprises,
   a) Mixing *Sesamum indicum* oil and Pig Fat in the ratio of 4:1;
   b) combining and adding extracts of *Curcuma longa* and *Glycyrrhiza glabra* in the ratio of 1:1 to step (a);
   c) adding extracts of *Hamiltonia suaveolens* in the ratio of 1:5 to step (a);
   d) adding extract of *Typha angustifolia* in the ratio of 1:10 to step (a);
   e) preparing *Azadirachta india* juice and is adding in the ratio of 1:5 to step (a) to obtain a mixture consisting of;
   *Sesamum indicum* oil and pig fat in 5 parts, *Curcuma longa* in 1 part and *Glycyrrhiza glabra* in 1 part, *Hamiltonia suaveolens* in 1 part, *Typha angustifolia* in 0.5 part, *Azadirachta india* juice in 1 part;
   f) evaporating the mixture of step (e) till the water is completely removed to obtain final formulation;
   g) fortifying the above formulation of step (f) 11 times using same herbal extracts in same proportions.

25. A method of treating a subject suffering from wounds, comprising administering herbal composition as a regenerative medicine according to claim 1.

26. The method according to claim 25, wherein said subject is mammal, including human.

27. The method of treating a subject suffering from wounds according to claim 25, wherein the wounds comprises open wounds including bed sores, burns, diabetic foot, post-operative wounds, leg ulcers, lower lip wounds, penile ulcers, urethral, scrotal, abdominal wounds and endoscopic wounds including prostate and urethral stricture wounds.

* * * * *